United States Patent [19]

Ü

[11] 4,341,218
[45] Jul. 27, 1982

[54] DETACHABLE BALLOON CATHETER
[75] Inventor: Ü, La Jolla, Calif.
[73] Assignee: University of California, Berkeley, Calif.
[21] Appl. No.: 147,020
[22] Filed: Mar. 6, 1980

Related U.S. Application Data

[63] Continuation of Ser. No. 910,310, May 30, 1978, abandoned.

[51] Int. Cl.³ ............................................. A61M 25/00
[52] U.S. Cl. ................................. 128/325; 128/349 B
[58] Field of Search ..................... 128/325, 348, 349 B, 128/350 R, 344, 129, 246; 285/97, 162, 196, 338

[56] References Cited

U.S. PATENT DOCUMENTS

| | | | |
|---|---|---|---|
| 3,190,679 | 6/1965 | Lester | 285/97 X |
| 3,395,710 | 8/1968 | Stratton et al. | 128/350 R |
| 3,799,170 | 3/1974 | Walsh et al. | 128/344 |
| 3,834,394 | 9/1974 | Hunter et al. | 128/325 |
| 4,085,757 | 4/1978 | Pevsner | 128/344 X |
| 4,130,119 | 12/1978 | Sessions et al. | 128/325 |

FOREIGN PATENT DOCUMENTS 2361123  4/1978  France ............................... 128/325

Primary Examiner—Dalton L. Truluck
Attorney, Agent, or Firm—Warren T. Jessup

[57] ABSTRACT

A detachable balloon catheter for easy placement in arterial lesions. The detachable balloon catheter is comprised of a balloon having a hollow cylinder securely fastened at the neck or entrance to the balloon. A catheter tube is held inside the cylinder by a releasable retainer which permits atraumatic detachment of the catheter tube after placement of the balloon in a lesion. A seal means is installed inside the balloon for sealing the balloon after its placement and inflation. The releasable retainer permits atraumatic detachment by complete separation of the catheter tube from the balloon and its withdrawal after placement of the balloon without any force being applied to the arterial lesion.

15 Claims, 8 Drawing Figures

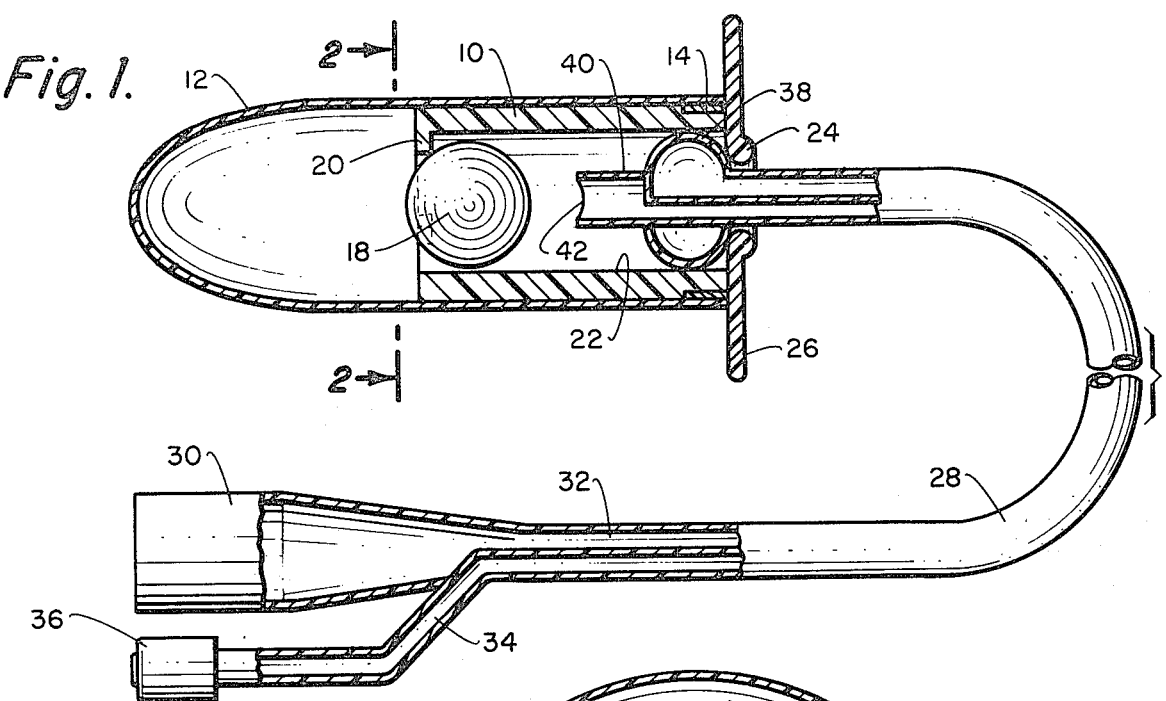
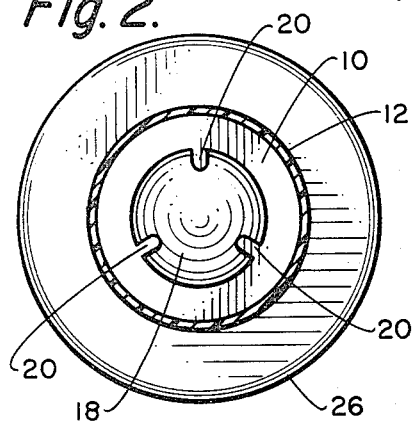
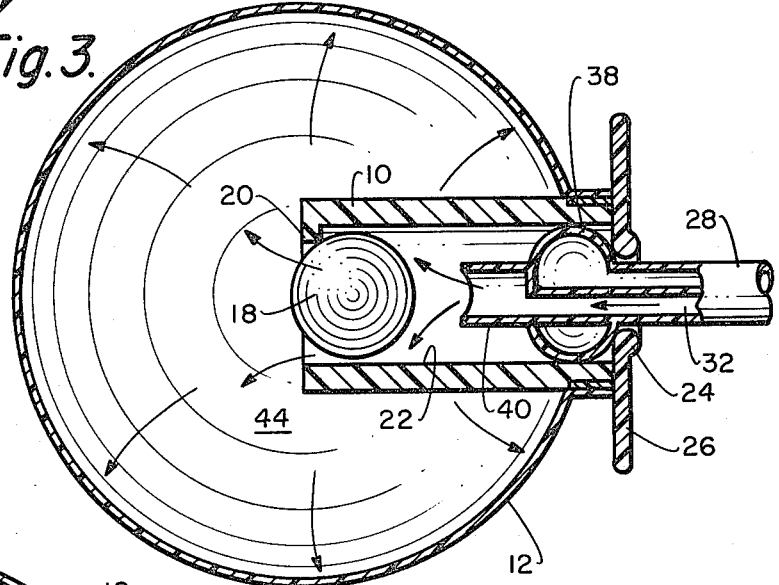
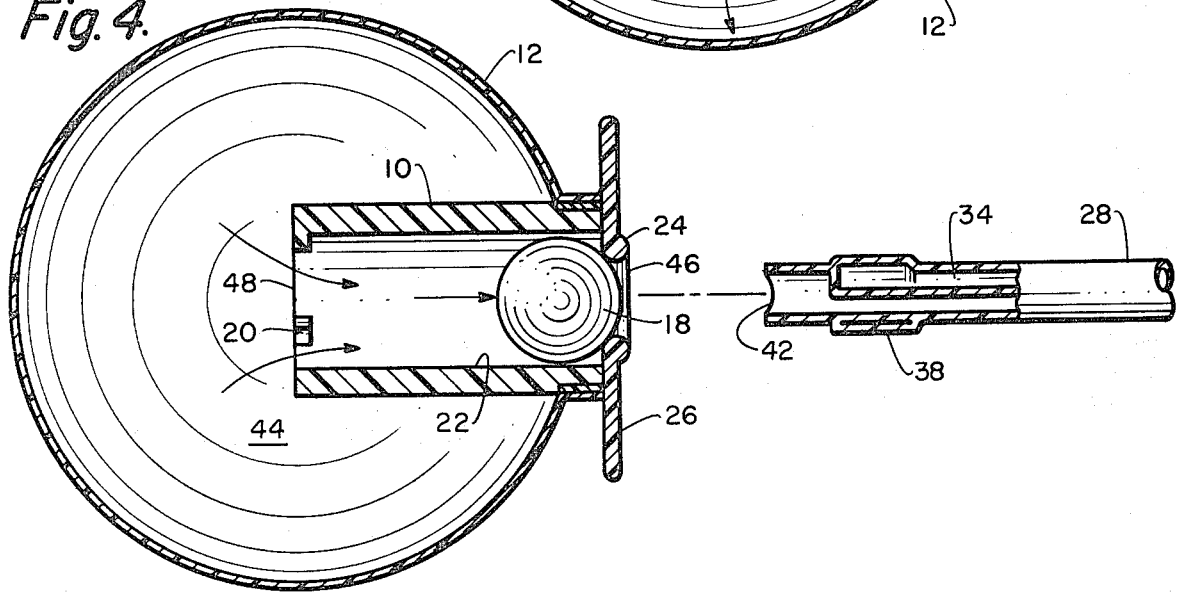

DETACHABLE BALLOON CATHETER

This is a continuation of application Ser. No. 910,310 filed May 30, 1978, now abandoned.

BACKGROUND OF THE INVENTION

This invention relates generally to catheters and more particularly to a detachable balloon catheter apparatus for the occlusion of arterial and arteriovenous lesions.

In the treatment of arterial lesions, and particularly those in the peripheral vascular system, traumatic vascular ruptures or fistulas traditionally require an operative procedure for repair in order that full functional capacity of the body part supplied be restored. Intracranial vascular anomalies, e.g. arteriovenous malformations (AVM), carotid-cavernous fistulas (co-fistulas) and arterial aneurysms also require extravascular operative interventions for repair and to protect adjacent vital brain structure from ischemia and destruction. Such procedures are frequently accompanied by a potentially high rate of morbidity and mortality. Thus, extravascular approaches to these problems are to a great extent unsatisfactory. Yet the only alternative of delay in such treatment is eventual irreparable damage. Recent innovations in the use of balloon catheters for intravascular non-operative treatment of these fistulas, and in one case an aneurysm, point to a potentially safe and atraumatic means of correction. In the case of the aneurysm, however, the neck portion was not occluded and this might permit eventual redevelopment of another lesion.

These lesions occur for a number of reasons. Trauma to the trunk or extremities can frequently cause arterial rupture with profuse blood loss, sometimes leading to exsanguination. Such lesions have been traditionally treated by open surgical exposure and repair by direct suturing or patching with a graft. Surgical repair of large or inaccessible vascular lesions has frequently been hampered by uncontrollable bleeding. It has been suggested, and in some cases demonstrated, that by using a balloon catheter, bleeding can be controlled intraoperatively. Nevertheless, the primary procedure is still one of open surgical exposure and repair under general anesthesia. Presently there is no way of occluding an arterial lesion or an arteriovenous fistula while preserving normal vascular potency without an operative procedure. The use of a one-unit balloon catheter with the catheter secured to the balloon at one end and leading out of the vascular lumen through an arterial puncture at the other end invariably will become complicated by the possibility of bleeding along the catheter and the risk of infection.

Carotid-cavernus fistulas, whether they be traumatic or of spontaneous origin, are usually treated by open surgical procedures in the neck or the head with thrombosis of the cavernous sinus or ligation of the carotid artery, or by occlusion of the cavernus carotid artery by balloon catheters. These procedures invariably result in the sacrifice of the internal carotid artery with the potential result of paralysis or even death. If left untreated, however, these fistulas can lead to blindness due to hypoxia to the retina.

Arterial aneurysms and arteriovenous malformations are usually congenital in origin and they are treated by extravascular and intravascular approaches. The extravascular approach is primarily an operative procedure called a craniotomy in which the arteriovenous lesion is removed or the arterial aneurysm occluded. Such procedures are very complicated and hazardous even in the best hands and especially in poor-risk patients. If left untreated, however, such lesions will eventually rupture, dooming the patient to disability and death. The introvascular route thus has been explored in the search for a safer and simpler therapeutic alternative. The intravascular route involves embolization of these lesions with an embolus or balloon carried to the lesion by the blood stream.

Studies have shown that an embolus/balloon at the end of a delicate, flexible catheter can be carried by the bloodstream to an aneurysm or arteriovenous malformation and be lodged there. These studies have particularly shown that an embolus held stationary at the intraluminal orifice of an aneurysm will be forced into the aneurysm and impacted there by the local hydrodynamic forces. In the case of the aneurysm, however, close examination of this means of treatment reveals that often the entire pathalogical process fails to be excluded from the normal circulation. In fact, frequently the weakened neck portion of the aneurysm remains open to the main circulation and continues to be subjected to the unceasing pulsating forces of the bloodstream. Thus, the exposed neck segments with their inherent defects can eventually expand to form another aneurysm or aneurysms capable of rupture, sometimes many years after the initial treatment. Therefore, none of the available techniques or means can reliably occlude these lesions from the main circulation safely, promptly and without an extensive operative procedure, while preserving the normal circulation.

SUMMARY OF THE INVENTION

The purpose of the present invention is to provide a detachable balloon catheter by which arterial or arteriovenous lesions can be treated by an intravascular route.

The detachable balloon catheter disclosed herein is simple and can provide safe occlusion of vascular lesions while preserving the main circulation from which they arise. The apparatus is comprised of a latex balloon having a cylinder secured in the neck of the balloon and means in the cylinder for sealing the balloon after inflation. In one case, a ball retained in the cylinder, free to slide from one end to the other, permits inflation of the balloon but yet provides a secure seal which is not easily dislodged, minimizing leakage from the balloon after inflation. Adjacent to the open end of the balloon is a flexible flange ring for sealing the balloon and cylinder by allowing the ball to press against it with the balloon inflated. Nodules, knobs, or protuberances at the interior end of the cylinder prevent the ball from being displaced out of the cylinder into the balloon when inflating the balloon. A double-lumened catheter may be inserted into the cylinder and retained in place by an expandable wall or second balloon on the end of the catheter tube which, when inflated, presses on the interior surface of the cylinder holding the tube of the catheter to the balloon. After placement and inflation of the balloon, the inflatable wall of the catheter tube may be deflated through a side lumen and the catheter tube withdrawn without any force being applied to the implanted balloon. The pressure in the balloon forces the ball against the ring seal after withdrawal of the catheter tube, effecting a tight seal. A circular flexible skirt extending outward from the end of the balloon/cylinder assembly is particularly useful in aneurysm cases as it covers and thus excludes the weakened neck region from the normal circulation.

In an alternative embodiment of the invention, a heat-expandable ring is secured inside the cylinder. The heat-expandable ring has a resistance electrode embedded in the expandable material for applying electrical current to heat and expand the ring. Electrical wires embedded in the side wall of the catheter tube permit the application of an electrical current from an external source to the electrode which is connected to these wires through fuse links. The catheter tube is therefore connected to the expandable ring (thus the balloon) by these fuse wire links which will melt when they reach a particular temperature for a length of time. The fuses are selected to have a temperature gradient such that the expandable ring completely seals the cylinder before the fuse links melt. The melting of the fuse wire then separates the end of the catheter tube from the balloon/cylinder assembly.

One object of the present invention is to provide a detachable balloon catheter apparatus which can occlude arterial and arteriovenous lesions.

Another object of the present invention is to provide a detachable balloon catheter apparatus in which the balloon can be placed in a lesion and the catheter tube withdrawn without trauma to the lesion.

Still another object of the present invention is to provide a detachable balloon catheter, the balloon part of which can be easily sealed after placement and inflation.

Yet another object of the present invention is to provide a detachable balloon catheter in which a catheter tube for inflating the balloon is releasably held onto the balloon until placement.

Still another object of the present invention is to provide a detachable balloon catheter having a flexible skirt for closing the neck of a lesion to prevent recurrence.

Other objects, advantages and novel features of the invention will become apparent from the following detailed description of the invention when considered in conjunction with the accompanying drawings wherein like reference numbers identify like parts throughout.

BRIEF DESCRIPTION OF THE DRAWINGS

FIG. 1 is a view of the detachable balloon catheter in partial section.

FIG. 2 is a view of the detachable balloon catheter of FIG. 1 taken at 2—2 of FIG. 1.

FIGS. 3 and 4 are sectional views illustrating the operation of the detachable balloon catheter of FIG. 1.

DETAILED DESCRIPTION OF THE PREFERRED EMBODIMENT

Figure 5:
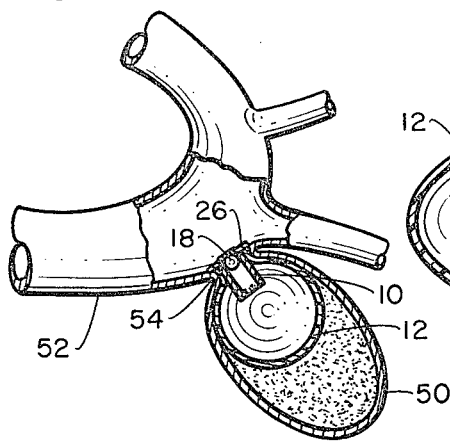
FIG. 5 is a view illustrating the use of a detachable balloon catheter of FIG. 1.

A detachable balloon catheter acccording to the invention is illustrated in FIG. 1. In this figure a cylinder 10 has a balloon 12 secured by an adhesive 14 at the base end of the cylinder 10. A ball 18 is retained at the internal end of the cylinder by stops 20 which may be in the form of any type of nodule or protuberance extending inward from the interior surface 22 of the cylinder 10. The ball 18 is slightly smaller than the internal diameter 22 of the cylinder 10, allowing it to freely slide from end to end of the cylinder and also allowing fluid injected through the catheter to flow around it into the balloon.

The opposite external end of the cylinder 10 has a flange ring 24 which can be integral with the cylinder or of a separate resilient material attached to the end of the cylinder 10 to prevent the ball from escaping the cylinder at this end. When the ball 18 is forced from the internal end of the cylinder 10 by pressure in the inflated balloon 12, the ball will be pushed against the flange ring 24, thus sealing the opening of the balloon. Extending outwardly from the flange ring 24 is a flexible skirt 26 which may be an integral part of the flange ring 24 or may be separately secured to the end of the cylinder 10. The purpose and function of the skirt 26 will be described in greater detail hereinafter.

A catheter tube 28 having a collar 30 for attaching a syringe for injection of a radio-opaque dye through a central lumen 32 is provided. The catheter tube 28 is a double lumen type having a second lumen 34 terminating in a collar 36 communicating with an expandable wall 38 similar to that used in a Foley catheter. The end 40 of the catheter tube passes freely into the cylinder 10 through the ring 24 and is releasably linked or coupled to and retained in the cylinder 10 by expansion of the balloon or expandable wall 38 of the catheter tube 28 by a physiologic fluid introduced through the side tubing 34. By this means the tube 28 is held fast to the cylinder 10 in fluid transfer relation with the balloon 12 but is not permanently attached thereto. The catheter tube 28 is used to deliver the balloon-catheter-cylinder assembly to a lesion.

The end 40 of the catheter tube 28 has a slight undercut portion 42 to avoid inadvertent sealing of the end of the tube against the ball 18.

The inflation of the balloon 12 through the tube 28 and withdrawl of the catheter tube 28 is illustrated in FIGS. 3 and 4. The balloon 12 is inflated by introducing a radio-opaque dye from a syringe fastened to collar 30 through the central lumen 32 into the interior of the balloon 44 expanding it as illustrated in FIG. 3. The radio-opaque dye, indicated by the arrows, flows around the ball into the balloon 12 while the ball is retained in the cylinder 10 by the stops 20. During this time the catheter tube 28 is retained in the cylinder 10 by the inflatable wall or second balloon 38.

Removal of the catheter tube is shown in FIG. 4 and is accomplished by deflating the tube or inflatable wall 38 by releasing the fluid through the side lumen 34. This reduces the diameter of the catheter tube 28 to less than the diameter of passageway 46 through the seal 24, thereby uncoupling tube 28 from cylinder 10 and permitting withdrawal of the catheter tube 28. Thus, the catheter tube 28 may be uncoupled without any relative movement between tube 28 and cylinder 10 or between tube 28 and balloon 12, and without applying any force such as pulling or tugging on the balloon/cylinder assembly or on the vascular lesion to which the balloon is secured. Simultaneously with withdrawal of the catheter tube 28, the radio-opaque dye 44 in the inflated balloon applies pressure against the ball 18, forcing the ball against the flange ring 24, sealing the passageway 46 out of the cylinder 10. Since the cylinder 10 at this point is only open at the end 48, potential leakage from the balloon is minimized. This is because the ball 18 cannot be substantially displaced from the seal 24, except in a direction along the axis of the tube 10, which only allows flow around the ball.

Placement of the balloon catheter in the manner illustrated in FIGS. 3 and 4 is shown in FIG. 5. For placement of the balloon catheter, an angiographic needle is introduced into the common carotid, femoral artery or other organic lumen through an arterial puncture. Through this needle the balloon catheter/balloon assembly is advanced into the bloodstream and carried into the circulation. The progress of the balloon catheter assembly is monitored, usually through X-ray, until the balloon is maneuvered to the fistula or aneurysm. The hemodynamic situation created by the flow in the bloodsteam at the site will cause the collapsed balloon to become lodged in the lesion 50 in the artery or organic lumen 52. The skirt 26 holds the balloon 12 at the opening of the fistula or neck 54 of the aneurysm 50. At this point the balloon 12 is inflated with a radio-opaque dye through the central lumen 32 to fill partially or completely the cavity of the aneurysm 50 or fistula. An arteriogram can then be taken to insure its complete exclusion from the main circulation. When complete exclusion is established, the catheter tube 28 is completely detached from the cylinder by deflation of the second balloon or inflatable wall 38. The catheter tube 28 may then be withdrawn from the cylinder and from the organic lumen 52, causing the pressure in the balloon to force the bead against the flange ring 24 to seal the end of the cylinder 10, as illustrated in FIG. 4. Thus, the balloon is maintained in an inflated condition and the ball 18 substantially prevents any leakage.

The entire procedure normally can be carried out under local anesthesia immediately after the angiographic diagnosis of the vascular lesion is made. In the case of the carotid cavenous fistula, no further blood shunting exists through the fistula which is completely occluded. In the case of the aneurysm 50, the entire pathologic specimen, including the defective neck 54, will be excluded from the main circulation in the artery 52. Since the cavity is substantially filled by the balloon, whatever blood remaining inside the cavity will clot.

Figure 6:
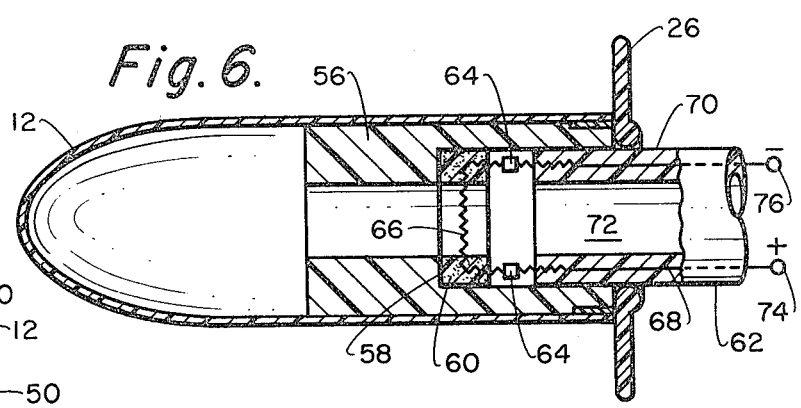
FIG. 6 is a sectional view of an alternative embodiment of the detachable balloon catheter.
Figure 7:
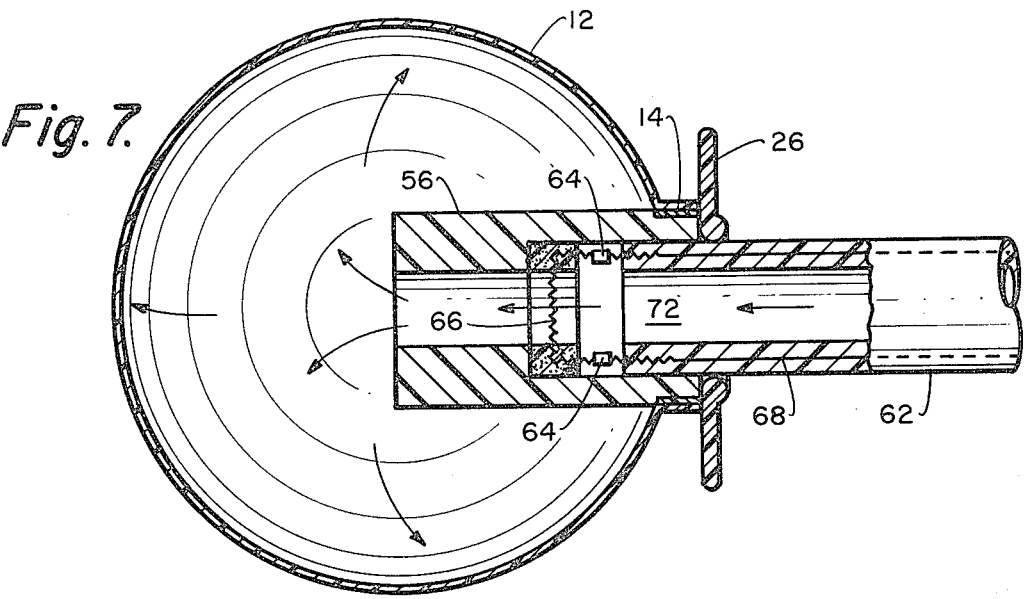
FIGS. 7 and 8 are sectional views illustrating the operation of the detachable balloon catheter of FIG. 6.
Figure 8:
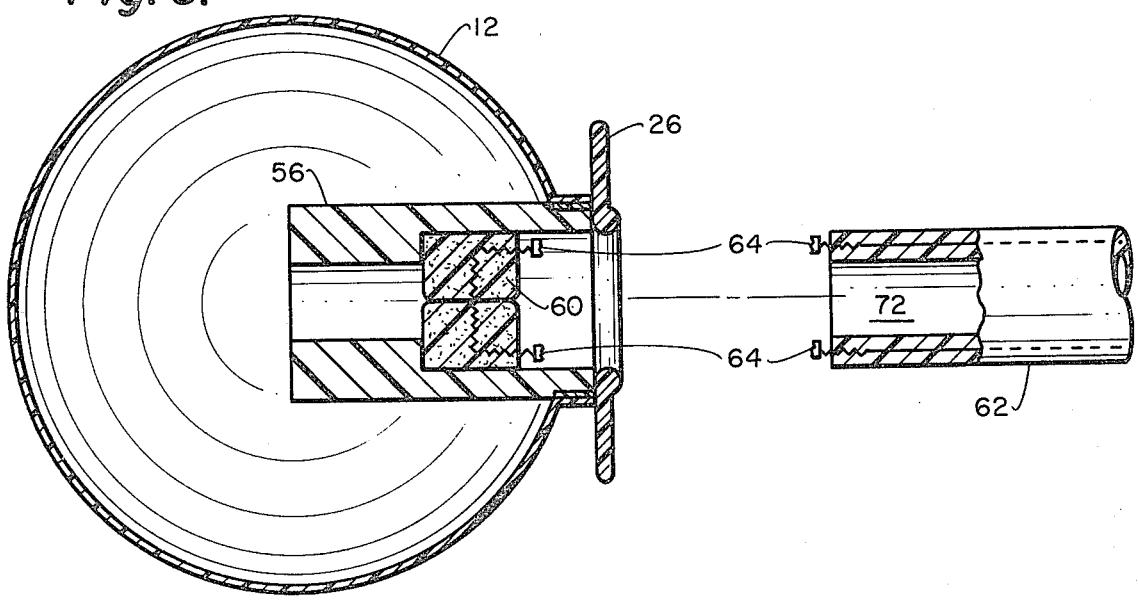

An alternative embodiment is illustrated in FIGS. 6 through 8. In this embodiment, the balloon 12 is attached to a metal cylinder 56 which has a stepped portion 58 which may be provided by a second cylinder inserted in the first, if desired. Secured inside the cylinder 56 is a band or ring of heat-expandable material 60. An electrode 66 is embedded in the heat-expandable material 60 and joined to a catheter tube 62 by fuse links 64. The fuse links 64 are connected to wires 68 passing through the wall 70 surrounding the main or central lumen 72 of the catheter tube 62. These wires 68 extend out through the end (not shown) of the catheter tube 62 ending in terminals 74 and 76 for applying electrical energy to the electrode 66. The cylinder 56 may be a three-ring arrangement with the outer ring being of high heat-resistant or metallic material. The balloon 12 is cemented securely by an adhesive 14 to the end of the cylinder 56. Preferably the heat-expandable material 60 will expand at temperatures in the range of 45° to 50° C. The cylinder 56 prevents expansion of the band of expandable material 60 outward. A flexible skirt 26 may be cemented to the end of ring 56 as before.

The method of using the embodiment illustrated in FIG. 6 is shown in FIGS. 7 and 8. The catheter tube 62 has an external diameter such that it easily slides in and out of the cylinder 56. The electrode 66 embedded in the material is such that it will heat the expandable band or ring 60 to completely close the cylinder 56, thus closing off the balloon 12 as illustrated in FIG. 8. The fuse links 64 are such that they will melt and separate at a temperature higher than that required to heat up the band 60 of expandable material to permit the band to completely seal the balloon opening. The band of expandable material may be of any suitable synthetic latex or a polymer such as a special polyurethane material. The fuse links, as indicated, need only be constructed of a material which will melt and separate at a temperature higher than the temperature at which the ring expands.

The balloon 12 and cylinder 56 assembly is delivered to the vascular malformation in the same manner as that for the embodiment illustrated in FIG. 1. After the balloon 12 is completely lodged in the vascular lesion and held in place at the opening by the flexible skirt 26, the balloon is inflated through the central lumen 72 to the desired volume with the radio-opaque dye as before. The complete closure of the lesion by the balloon 12 is then confirmed by angiography as before. At this point electricity is applied to terminals 74 and 76, causing electrode 66 to heat and expand the band or ring 60. The ring 60 will then expand to seal the opening of the cylinder 56 as illustrated in FIG. 8. Continued heating through the wires 68 to a higher temperature will continue to cause expansion of the ring 60, creating a leak-tight seal of the balloon opening and will also cause a separation of the fuse links 64, breaking the connection betwen the catheter tube 62 and the balloon assembly. The catheter may then be withdrawn leaving behind the inflated and sealed balloon 12 which now completely closes off the vascular lesion. The method and apparatus described herein will not only obviate any operative procedure, but also will insure the intravascular exclusion of the entire pathological process from the main circulation immediately preventing if from causing any serious damage.

Obviously, many modifications and variations of the present invention are possible in light of the above teachings. It is therefore to be understood that the full scope of the invention is not limited to the details disclosed herein, but may be practiced otherwise than as specifically described.

What is claimed is:

1. A detachable balloon catheter adapted to be placed in an organic lumen, comprising:
   a balloon having a neck portion;
   a cylinder secured to the neck portion of said balloon;
   a catheter tube;
   means mounted on the distal end of said tube for coupling said tube to said cylinder in fluid transfer relation with said balloon for inflating said balloon through said cylinder, by initially securing said tube end within said cylinder; and
   for uncoupling said tube from said cylinder, without any relative movement between said tube and said cylinder or between said tube and said balloon, whereby said tube may be released from said cylinder atraumatically and withdrawn from the lumen without the application of force to said cylinder or to said balloon;
   seal means for sealing said cylinder substantially simultaneously with withdrawal of said tube.

2. The apparatus according to claim 1 wherein said seal means comprises:
   a ball in said cylinder free to slide to either end;
   stop means for stopping said ball from exiting said cylinder at the balloon end of said cylinder;
   a resilient flange ring at the opposite end of said cylinder for sealing against said ball when said tube is withdrawn, thereby maintaining inflation of said balloon.

3. The apparatus according to claim 2 including:
a flexible circular skirt on the end of said cylinder for closing off the entrance to a lesion.

4. The apparatus according to claim 1 wherein said sealing means comprises:
a heat-expandable material in said cylinder;
heat means for heating said material to expand and close off said cylinder.

5. The appparatus according to claim 4 wherein said heat-expandable material compirses a ring of material inside said cylinder.

6. The apparatus according to claim 5 wherein said heating means comprises:
an electrode embedded in said ring of expandable material;
electrical means for applying an electrical current to said electrode to heat said expandable material.

7. The apparatus according to claim 6 wherein said electrical means comprises an electrical wire passing through said catheter tube connected to said electrode.

8. The apparatus according to claim 7 wherein said means for separating said catheter tube comprises:
fuse wires connecting the wire in said catheter tube to the electrode in said expandable material;
said fuse wire having a temperature gradient selected to break fuse, separating the tube from the said expandable material, thus the balloon/cylinder assembly, after the cylinder has been sealed.

9. A detachable balloon catheter apparatus comprising:
a balloon having a neck portion;
a hollow cylinder secured in the neck portion of said balloon;
a ball in said cylinder having an outside diameter slightly smaller than the inside diameter of said cylinder so that the ball may slide freely in said cylinder;
retaining means on the interior end of said cylinder for retaining said ball in said cylinder;
seal means at the opposite end of said cylinder for sealing against said ball;
a double-lumened catheter tube having a main lumen and a side lumen, with its end passing through said seal means into said cylinder for inflating said balloon;
holding means for maintaining said ball spaced from said seal means;
means for uncoupling the end of said tube from said cylinder before any withdrawal movement is made;
whereby said catheter tube may be easily and atraumatically removed after inflating said balloon;
withdrawal of said tube disabling said holding means;
whereby upon withdrawal of said tube said ball may seal against said seal means.

10. The catheter according to claim 10 wherein said retaining means comprises:
a plurality of protuberances on the inside surface of said cylinder;
said protuberances acting to retain the ball while permitting fluid flow around the ball into the balloon.

11. The catheter according to claim 9 including:
a planar flexible skirt on said tube coaxially with said seal.

12. The catheter according to claim 11 wherein said skirt is an outward extension of said seal.

13. The catheter according to claim 9 including:
an inflatable wall in the end of said tube;
said inflatable wall being in communication with said side lumen for inflation;
whereby expansion of said inflatable wall causes said wall to expand to a size larger than the passageway through said seal means and to press against the inside of said cylinder coupling said tube to said cylinder.

14. The catheter according to claim 13, including deflating means for deflating said expandable wall, thereby uncoupling said tube from said cylinder.

15. A detachable balloon catheter comprising:
a balloon having a neck portion;
a cylinder secured in the neck portion of said balloon;
a catheter tube for inflating said balloon through said cylinder and adapted to be inserted into and through a lumen;
releasable coupling means for releasably coupling the end of said tube to said cylinder, said releasable coupling means comprising inflatable wall means near the end of said tube and a side lumen in said tube for inflating said wall means to retain said tube in said cylinder during placement, and for deflating said wall means to uncouple said tube from said cylinder atraumatically before any withdrawal movement of said tube is made;
seal means for sealing said cylinder substantially simultaneously with the withdrawal of said tube;
whereby said tube may be separated from said cylinder and removed from the lumen after placement of said balloon.

* * * * *